United States Patent [19]

Steffee

[11] Patent Number: 4,655,199

[45] Date of Patent: Apr. 7, 1987

[54] SPINAL COLUMN STRAIGHTENING APPARATUS

[75] Inventor: Arthur D. Steffee, Moreland Hills, Ohio

[73] Assignee: AcroMed Corporation, Cleveland, Ohio

[21] Appl. No.: 717,954

[22] Filed: Mar. 29, 1985

[51] Int. Cl.⁴ .............................................. A61F 5/04
[52] U.S. Cl. ................................ 128/69; 128/92 YM; 128/92 YF
[58] Field of Search ..................... 128/69, 92 R, 92 B, 128/75, 78, 92 YF, 92 YE, 92 YM

[56] References Cited

U.S. PATENT DOCUMENTS

| 3,242,922 | 3/1966 | Thomas | 128/92 R |
| 3,693,616 | 9/1972 | Roaf et al. | 128/69 |
| 4,448,191 | 5/1984 | Rodnyansky et al. | 128/69 |
| 4,456,005 | 6/1984 | Lichty | 128/92 B X |
| 4,493,317 | 1/1985 | Klaue | 128/92 B X |

FOREIGN PATENT DOCUMENTS

| 2806414 | 10/1978 | Fed. Rep. of Germany | 128/92 B |
| 1243353 | 8/1971 | United Kingdom | 128/69 |
| 876125 | 10/1981 | U.S.S.R. | 128/92 B |

OTHER PUBLICATIONS

French Article, "Rhamatisme Vertebra" (Roy-Camille et al.).

Primary Examiner—Edgar S. Burr
Assistant Examiner—Moshe I. Cohen
Attorney, Agent, or Firm—Tarolli, Sundheim & Covell

[57] ABSTRACT

An apparatus for maintaining a desired spatial relationship between adjacent vertebrae and the sacrum includes a spinal plate which engages both the sacrum and vertebrae. The spinal plate is connected with the vetebrae and the sacrum by fastener assemblies. In order to enable a fastener assembly to engage the relatively thin sacrum, a fixture is connected with the spinal plate to enable the fastener which engages the sacrum to be skewed at an acute angle. The fixture has a mounting end portion which is slidably received in a slot in the spinal plate and a head end portion through which the fastener assembly extends.

8 Claims, 10 Drawing Figures

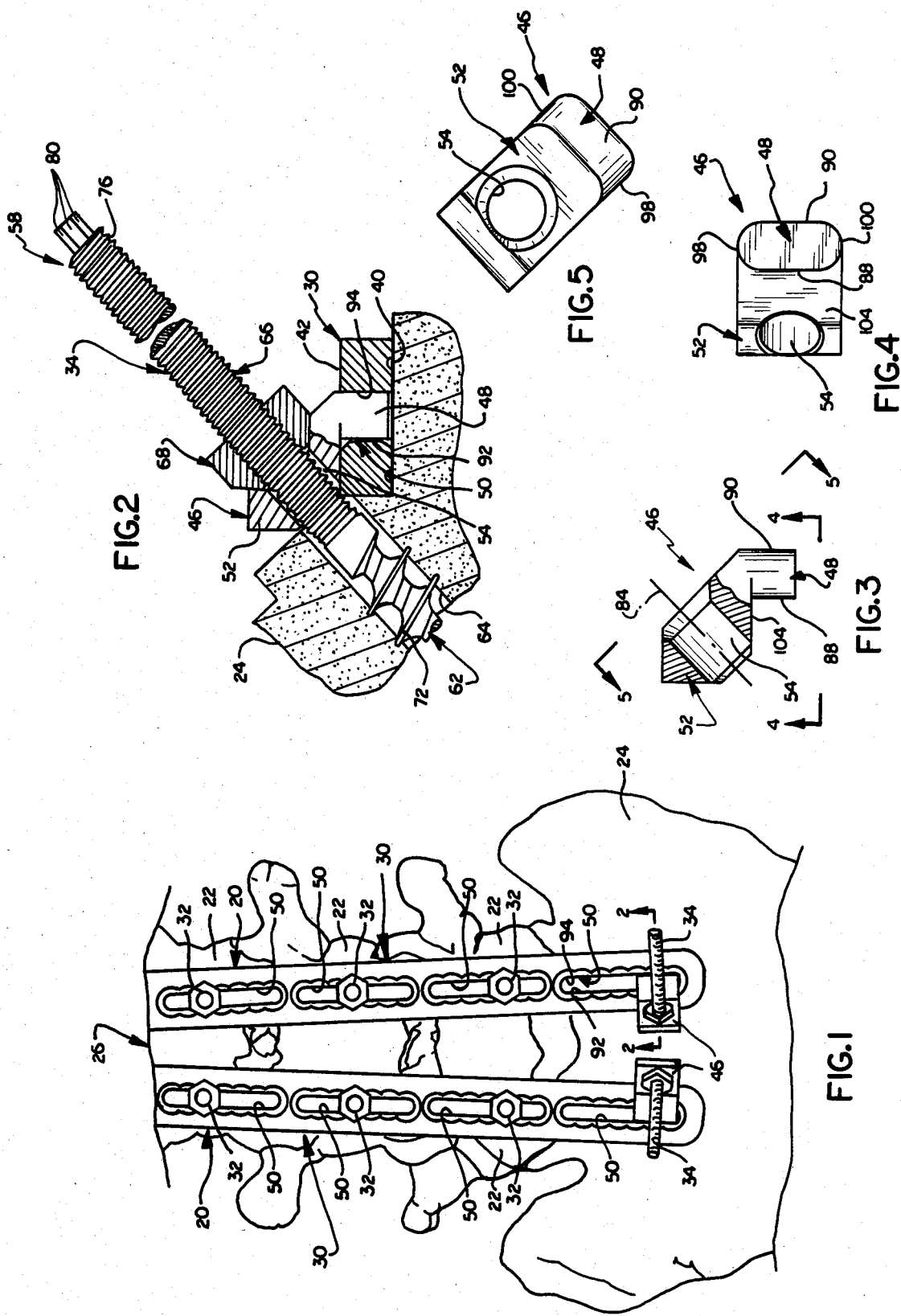

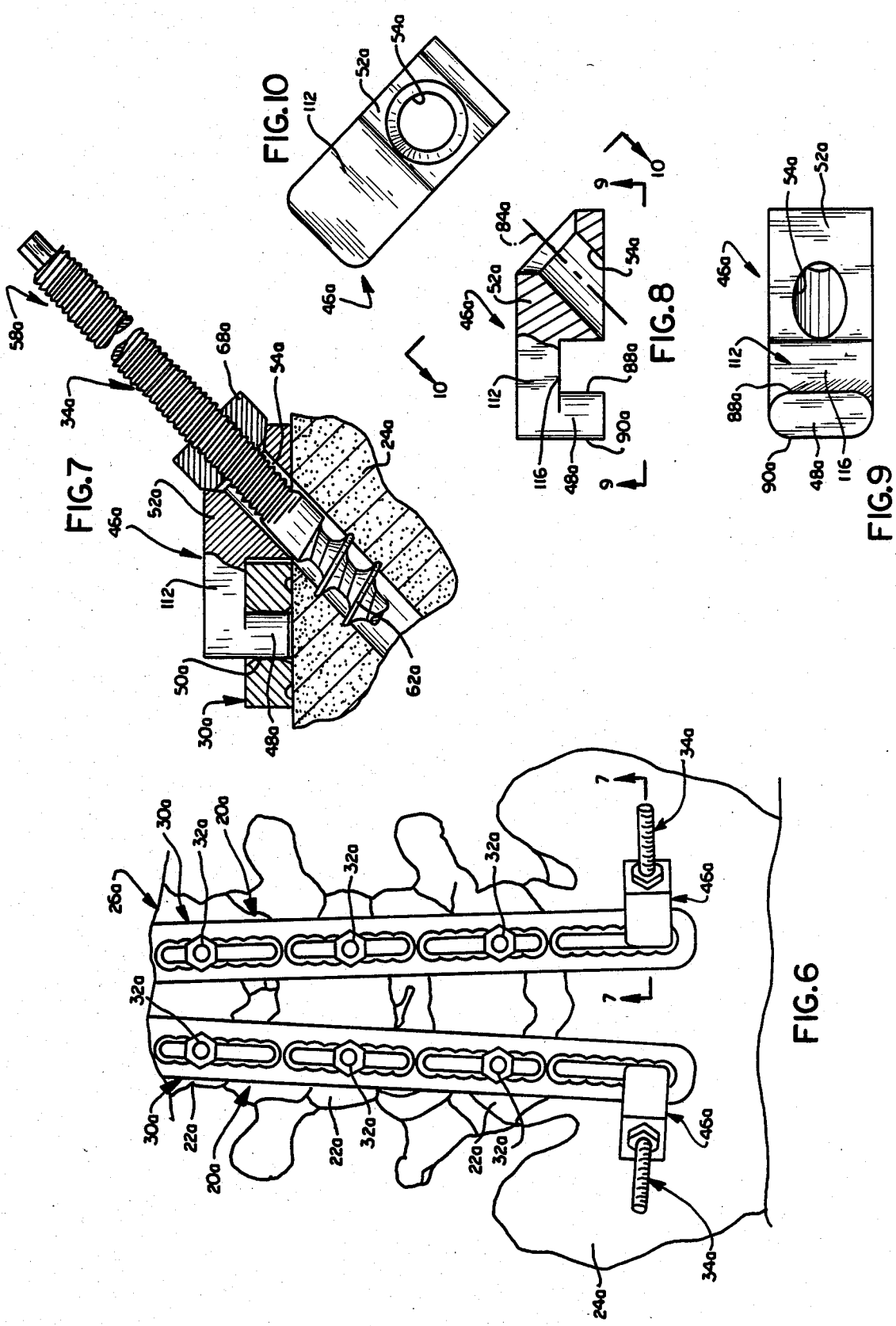

SPINAL COLUMN STRAIGHTENING APPARATUS

BACKGROUND OF THE INVENTION

The present invention relates to an apparatus for straightening a spinal column and more particularly to an apparatus which maintains a desired spatial relationship between adjacent vertebrae and the sacrum.

An article entitled "Rhamatisme Vertebra" by Roy-Camille, Sailliant and Judet discloses the use of a rigid plate to hold adjacent vertebrae and the sacrum in a desired spatial relationship. When the rigid plate is to be mounted on the spinal column, accurately located holes are drilled in the vertebrae and the sacrum. Holes in the plate are then positioned in alignment with the holes in the vertebrae and sacrum. Screws are then twisted into the vertebrae and sacrum to clamp them to the plate. The screws extend perpendicular to the plate.

Due to the relatively thin construction of the sacrum, one or more of the screws may extend through the sacrum unless the screws are very accurately positioned and the length of the screws carefully selected to be less than the thickness of the sacrum. Of course, if a screw extends through the sacrum, the body organs on the opposite side of the sacrum could be injured by the screw.

U.S. Pat. No. 4,047,523 discloses an L-shaped sacral anchor that is used to secure a cable to the sacrum in carrying out a scoliosis correction operation. One leg of the L-shaped anchor consists of two prongs which are inserted in the disc space between two sacral vetebrae. The other leg is a bridge portion that connects the two prongs and which has a collet formed integrally therewith for receiving a cable.

SUMMARY OF THE PRESENT INVENTION

The present invention provides a new and improved apparatus for maintaining a desired spatial relationship between adjacent vertebrae and the sacrum. The apparatus includes an elongated spinal plate which engages the vetebrae and the sacrum. Fasteners extend through openings in the plate to connect the plate with the vertebrae. A fixture projects from the plate and positions a fastener so that it is skewed at an acute angle to the sacrum. The angle at which the fastener engages the sacrum allows the fastener to securely grip the relatively thin sacrum without extending through the sacrum.

The spinal plate has elongated slots through which the fasteners extend into engagement with the vertebrae. The slots allow the relative position of the fasteners and plate to be selected to optimize the area of engagement of the fasteners with the vertebrae. The fixture is slidably mounted in one of the slots in the spinal plate. This allows the fixture to be moved along the slot to optimize the position at which a fastener extends through the fixture into engagement with the sacrum.

In one embodiment of the invention, the fixture positions a fastener so that it slopes outwardly away from the spinal plate to engage the sacrum only at locations which are offset to one side of the spinal plate. In another embodiment of the invention, the fixture positions a fastener so that it slopes inwardly at an acute angle toward the plate so that the fastener extends into a portion of the sacrum beneath the plate. By selecting the proper one of the two fixtures, the orientation of the fastener relative to the sacrum can be optimized.

Accordingly, it is an object of this invention to provide a new and improved apparatus for maintaining a desired spatial relationship between adjacent vertebrae and the sacrum and wherein a fixture projects from a plate which engages the vertebrae and sacrum and positions a fastener so that it is skewed at an acute angle to the relatively thin sacrum without piercing the sacrum.

BRIEF DESCRIPTION OF THE DRAWINGS

The foregoing and other objects and features of the present invention will become more apparent upon a consideration of the following description taken in connection with the accompanying drawings wherein:

FIG. 1 is a fragmentary dorsal view of a portion of a vertebral or spinal column on which an apparatus constructed in accordance with the present invention has been installed to maintain a desired spatial relationship between adjacent vertebrae and the sacrum;

FIG. 2 is an enlarged fragmentary sectional view, taken along the line 2—2 of FIG. 1, depicting the manner in which a fixture mounted on a spinal plate positions a fastener relative to the sacrum;

FIG. 3 is a fragmentary elevational view of the fixture of FIG. 2;

FIG. 4 is a bottom plan view, taken generally along the line 4—4 of FIG. 3, further illustrating the construction of the fixture;

FIG. 5 is a side elevational view, taken generally along the line 5—5 of FIG. 3, further illustrating the construction of the fixture;

FIG. 6 is a fragmentary dorsal view of a portion of a vertebral or spinal column upon which a second embodiment of an apparatus constructed in accordance with the present invention has been installed to maintain a desired spatial relationship between adjacent vertebrae and the sacrum;

FIG. 7 is an enlarged fragmentary sectional view, taken along the line 7—7 of FIG. 6, depicting the manner in which a second embodiment of the fixture is mounted on a spinal plate to position a fastener relative to the sacrum;

FIG. 8 is an elevational view of the fixture of FIG. 7;

FIG. 9 is a bottom plan view, taken generally along the line 9—9 of FIG. 8, further illustrating the construction of the fixture; and FIG. 10 is a side elevational view, taken generally along the line 10—10 of FIG. 8, further illustrating the construction of the fixture.

DESCRIPTION OF SPECIFIC PREFERRED EMBODIMENTS OF THE INVENTION

General Description

A pair of assemblies 20 for maintaining a desired spatial relationship between adjacent vertebrae 22 and the sacrum 24 are illustrated in FIG. 1 installed on a person's vertebral or spinal column 26. Each of the assemblies 20 includes an elongated spinal plate 30 which is mounted on the vertebrae 22 by a plurality of identical fastener assemblies 32. Each stainless steel spinal plate 30 is also mounted on the sacrum 24 by fastener assemblies 34 which have the same construction as the fastener assemblies 32.

The illustrated spinal plate 30 has a length so as to extend from the sacrum 24 and span more than three adjacent vertebrae 22. A pair of fastener assemblies 32 is provided for each vertebra 22 to connect it with each of the spinal plates 30. In addition, a pair of fastener assemblies 34 is provided for the sacrum 24 to connect it with each of the spinal plates 30.

The assemblies 20 are installed to maintain a desired spatial relationship between adjacent vetebrae 22 and sacrum 24. When the assemblies 20 are to be installed, the sharp blunt spinous processes which project from the vertebrae 22 and sacrum 24 are removed. A pair of series of vertically aligned holes are then drilled in the vertebrae 22. In addition, a pair of holes are drilled in the sacrum 24. The fastener assemblies 32 and 34 are then mounted in the holes in the vertebrae 22 and sacrum 24.

The spinal plates 30 are then positioned relative to the fastener assemblies 32 and 34. The fastener assemblies 32 and 34 are then tightened against the spinal plates 30 to pull the vertebrae 22 and sacrum 24 into a desired spatial relationship. The fastener assemblies 32 and 34 cooperate with the vertebrae 22, sacrum 24 and spinal plates 30 to maintain the vertebrae and sacrum in the desired spatial relationship.

In accordance with a feature of the present invention, the fastener assemblies 34 which connect the spinal plates 30 with the sacrum 24 are skewed relative to the spinal plates and sacrum (see FIG. 2). Skewing the fastener assemblies 34 relative to the spinal plates 30 enables the fastener assemblies to engage the sacrum 24 throughout a relatively long length without piercing or extending through the sacrum (see FIG. 2). Thus, if the fastener assemblies 34 extended perpendicular to inner and outer major sides 40 and 42 of the spinal plate 30, there is a possibility that the fastener assemblies would extend through the relatively thin sacrum 24 and would damage body organs on the opposite side of the sacrum.

By skewing the fastener assemblies 34 at an acute angle relative to the sacrum 24, the fastener assemblies can extend further into the sacrum with less danger of extending through the sacrum. In order to skew a fastener assembly 34 relative to a spinal plate 30 and the sacrum 24, a fixture 46 projects from the spinal plate 30 and positions the fastener assembly 34 in a skewed orientation.

The fixture 46 (FIG. 2) includes a mounting end portion 48 which is received in one of a plurality of elongated slots 50 formed in the spinal plate 30. In addition to the mounting end portion 48, the fixture 46 has a head end portion 52 with an opening 54 which positions the fastener assembly 34 in a skewed orientation to maximize the extent of engagement of the fastener assembly with the sacrum 24. Since the mounting end portion 48 of the fixture 46 is received in the slot 50, the fixture can be moved axially along the slot to locate the opening 54 and fastener assembly 34 in a desired position relative to the sacrum.

Spinal Plate

Each of the spinal plates 30 has a plurality of longitudinally extending slots 50. The identical slots 50 have longitudinal axes which are coincident with the longitudinal axis of the spinal plate 30. The equally spaced slots 50 have bevelled edge portions which cooperate with the fastener assemblies 32 and 34.

The inner or bottom side 40 (FIG. 2) of a spinal plate 30 is provided with a plurality of grooves. The grooves prevent sliding of the spinal plate relative to the vertebrae 22 and sacrum 24. In addition the bony material of the vertebrae 22 and sacrum 24 tends to grow into the grooves in the bottom of the spinal plate 30 to further hold the spinal plate against movement relative to the vertebrae and sacrum. The construction of the spinal plate 30 is the same as is disclosed in U.S. patent application Ser. No. 562,438 filed Dec. 16, 1983 by Arthur B. Steffee and entitled "Apparatus for Straightening Spinal Columns".

Fastener

Each of the identical fastener assemblies 34 includes an axially extending force transmitting member 58 (FIG. 2). The force transmitting member 58 has a mounting end portion 62 which is received in a cylindrical hole 64 drilled in the sacrum 24 and a retaining end portion 66 which engages a nut 68. The force transmitting member 58 extends through the cylindrical opening 54 formed in the head end portion 52 of the fixture 46. When the nut 68 is tightened, the spinal plate 30 and head end portion 52 of the fixture 46 are pressed against the outer side surface of the sacrum. The outer side surface of the sacrum 24 has been shaped to receive the spinal plate 30 and to engage the head end portion 52 of the fixture 41.

The mounting end portion 62 of the force transmitting member 58 is provided with a relatively large diameter helix 72. When the force transmitting member 58 is pressed axially into the hole 64 in the sacrum 24 and rotated, the helix 72 screws itself into the hole. The helix 72 has a substantially larger crest diameter than the inside diameter of the hole 64 so that the helix cuts into the cylindrical side surface of the hole to firmly mount the force transmitting member 58 in the sacrum 24.

The retaining end portion 66 of the force transmitting member 58 has an external screw thread 76 which engages a standard internal thread formed in the nut 68. The nut 68 has wretching flats which are gripped by a suitable wrench to rotate the nut relative to the external thread 76. During rotation of the nut 68, the force transmitting member 58 is held against rotation by engaging wrenching flats 80 on an outer end portion of the force transmitting member. As the nut 68 is rotated, the spinal plate 30 and head end portion 52 of the fixture 46 are pressed firmly against the sacrum 24.

The fastener assemblies 32 for connecting the spinal plate 30 with the vertebrae 22 have the same construction as the fastener assembly 34. The specific construction of the fastener assembly 34 is more fully described in co-pending U.S. patent application Ser. No. 562,438 filed Dec. 16, 1983 by Arthur B. Steffee and entitled "Apparatus for Straightening Spinal Columns".

Fixture

The fixture 46 positions the fastener assembly 34 so that it is skewed at an acute angle to a plane containing the longitudinal central axis of the spinal plate 30 and the central axes of the fastener assemblies 32 which connect the spinal plate 30 with the vertebrae 22. In the specific embodiment of the fixture 46 illustrated in FIGS. 2-5, the opening 54 is oriented with a central axis 84 (FIG. 3) extending at an angle of 45° to the plane which contains the central axis of the mounting plate 30 and the central axes of the fastener assemblies 32 which are connected with the vertebrae 22. The orientation of the head end portion 52 is such that the fastener assembly 34 extends sidewardly from the spinal plate 30 and engages the sacrum 24 along a path which is offset to one side of the spinal plate.

The mounting portion 48 of the fixture 46 has a pair of parallel flat side surfaces 88 and 90 which engage opposite side surfaces 92 and 94 of a spinal plate slot 50 (see FIGS. 1 and 2). The parallel side surfaces 88 and 90 on the mounting portion 48 of the fixture 46 cooperate with the parallel longitudinally extending sides 92 and 94 of the slot 50 to hold the fixture against rotational movement relative to the slot 50. The distance between opposite arcuate ends 98 and 100 of the mounting portion 48 (see FIG. 4) of the fixture 46 is substantially less than the length of the slot 50. This enables the fixture 46 to be moved axially along the slot 50 until the fixture 46 is positioned in a desired location relative to the sacrum 24.

The head portion 52 of the fixture 46 is provided with a flat inner side surface 104 (FIGS. 3 and 4) which abuttingly engages the upper or outer side 42 (FIG. 2) of the spinal plate 30. The width of the surface 104 is such that the inner edge of the opening 54 is disposed adjacent to an outer corner of the spinal plate 30 (FIG. 2). This enables the fastener assembly 34 to extend through the opening 54 in the fixture 46 into engagement with the sacrum 24. Since the longitudinal central axis of the fastener assembly 34 is skewed at an angle of approximately 45° with the opposite sides of the sacrum 24, the distance which the fastener can engage the sacrum without extending through the sacrum is substantially greater than would be the case if the fastener 34 extended perpendicular to the opposite sides of the sacrum.

Although the fixture 46 has been oriented with the fastener assembly 34 projecting toward the left in FIG. 2, the mounting end portion 48 of the fixture 46 could be disposed in the slot 50 with the head end portion 52 extending to the right (as viewed in FIG. 2). This would result in the fastener assembly 34 extending rightwardly from the spinal plate 30 into engagement with the sacrum 24.

Installation

When the assemblies 20 are to be installed on a vertebral column, the spinuous processes are removed from the vertebrae 22 and sacrum 24 upon which the assemblies are to be mounted. Holes are then drilled at carefully selected locations in the adjacent vertebrae 22. In addition, a pair of holes 64 are drilled in the sacrum 24. The central axes of the holes 64 drilled in the sacrum 24 are skewed at an angle of 45° to the axes of the holes drilled in the vertebrae 22.

Force transmitting members of the fastener assemblies 32, that is the force transmitting members corresponding to the force transmitting members 58 of the fastener assembly 34, are mounted in the holes in the vertebrae 22. In addition, the force transmitting members 58 for the fastener assemblies 34 are mounted in the axially skewed holes 64 in the sacrum 24.

To mount the force transmitting members in the holes 64 in the sacrum 24, torque is applied to the wrenching flates 80 on the outer end portions of the force transmitting members 58 while they are pressed into the holes. The helix 72 on the leading end of the force transmitting member 58 cuts into the inner side of the opening 64 and is screwed into the opening. The force transmitting members for the fastener assemblies 32 are mounted in the openings in the vertebrae 22 in the same manner.

Once the force transmitting members 58 for the fastener assemblies 32 and 34 have been mounted in the vertebrae 22 and sacrum 24 in the manner previously explained, the spinal plates 30 are positioned with the force transmitting members for fastener assemblies 32 extending through slots 50 in the spinal plate. At the same time, the outer end portion 66 of the force transmitting members 58 are inserted through the openings 54 in the head end portions 52 of the fixtures 46. The mounting end portions of the fixtures 46 are received in slots 50 in the spinal plates 30.

Once the inner side 40 of the spinal plate 30 has been positioned in flat abutting engagement with the vertebrae 22 and sacrum 24, the nuts 68 are turned onto the threaded end portions 66 of the fastener assemblies 34 to press the head end portions 52 of the fixtures 46 and the spinal plate 30 inwardly against the sacrum 24. In addition, the nuts for the fastener assembly 32 are tightened to press the inner side surface 40 of the spinal plate 30 into firm abutting engagement with the vertebrae 22.

Second Embodiment of the Invention

In the embodiment of the invention illustrated in FIGS. 1-5, the fastener assemblies 34 slope outwardly away from the spinal plate 30 to engage the sacrum 24 only at locations which are offset to one side of the spinal plate. It is contemplated that it may be desireable that the fastener assemblies engage the sacrum 24 at locations disposed inwardly of the spinal plate 30. Therefore, in the embodiment of the invention illustrated in FIGS. 6-10, the fixtures position the fastener assemblies so that they extend through holes in the sacrum at locations beneath the spinal plates. Since the embodiment of the invention illustrated in FIGS. 6-10 is generally similar to the embodiment of the invention illustrated in FIGS. 1-5, similar numerals will be utilized to designate similar components, the suffix letter "a" being associated with the embodiment of the invention shown in FIG. 6 in order to avoid confusion.

The assemblies 20a for maintaining a desired spatial relationship between adjacent vertebrae 22a and the sacrum 24a is illustrated in FIG. 6. Each of the assemblies 20a includes an elongated rigid spinal plate 30a which is mounted on the vertebrae 22a by a plurality of identical fastener assemblies 32a. The spinal plates 30a are mounted on the sacrum 24a by fastener assemblies 34a.

The fastener assemblies 34a for connecting the spinal plate 30a with the sacrum 24a extend through an opening 54a formed in the head end portion 52a of a fixture 46a (see FIG. 7). The fixture 46a is connected with a spinal plate 30a by a mounting end portion 48a which extends into a slot 50a formed in the spinal plate 30a.

In accordance with a feature of the embodiment of the invention shown in FIGS. 6-10, the longitudinal central axis of a force transmitting member 58a of the fastener assembly 34a slopes inwardly toward the spinal plate 30a. To provide for this orientation of the force transmitting member 58a, the head end portion 52a of the fixture 46a is connected with the mounting portion 48a of the fixture by a body or connector portion 112. The connector portion 112 extends across a side section of the spinal plate 30a so that the head end portion 52a of the fixture is disposed to one side of the spinal plate 30a. The force transmitting member 58a extends inwardly toward the spinal plate 30a so that the helical mounting end portion 62a of the force transmitting member 58a is disposed inwardly of the spinal plate 30a (see FIG. 7). When the nut 68a is tightened, the head end portion 52a of the fixture 46a is pressed firmly against the sacrum 24a along with the spinal plate 30a.

The longitudinal central axes of the fastener assemblies 32a which connect the spinal plates 30a with the vertebrae 22a (FIG. 6) extend perpendicular to and intersect the longitudinal central axis of the spinal plate 30a and are therefore disposed in a single plane. The longitudinal central axis of the force transmitting member 34a is skewed at an acute angle to the plane which contains the central axis of the fastener assemblies 32a and the central axis of the spinal plate 30a.

The mounting section 48a of the fixture 46a has a pair of parallel side surfaces 88a and 90a which engage opposite sides of the slot 50a in the spinal plate 30a. The fixture 46a can be moved axially along the slot 50a to enable the position of the fixture 46a to be adjusted relative to the sacrum.

The connector section 112 of the fixture 46a has a flat bottom or inner side surface 116 which abuttingly engages the outer side of the spinal plate 30a. The central axis 84a of the opening 54a in the head end portion 52a of the fixture 46a is skewed, in the illustrated embodiment of the invention, at an angle of 45° relative to the plane which contains the longitudinal axis of the spinal plate 30a and the axes of the fastener assemblies 32a.

SUMMARY

The present invention provides a new and improved apparatus 20 for maintaining a desired spatial relationship between adjacent vertebrae 22 and the sacrum 24. The apparatus 20 includes an elongated spinal plate 30 which engages the vertebrae and the sacrum 24. Fastener assemblies 32 extend through openings in the plate 30 to connect the plate with the vertebrae 22. A fixture 46 projects from the spinal plate 30 and positions a fastener assembly 34 so that it is skewed at an acute angle to the sacrum 24. The angle at which the fastener assembly 34 engages the sacrum 24 allows the fastener assembly to securely grip the relatively thin sacrum without extending through the sacrum.

The spinal plate 30 has elongated slots 50 through which the fastener assemblies 32 extend into engagement with the vertebrae 22. The slots 50 allow the relative position of the fastener assemblies 32 and spinal plate 30 to be selected to optimize the area of engagement of the fastener assemblies with the vertebrae. The fixture 46 is slidably mounted in one of the slots 50 in the spinal plate 30. This allows the fixture 46 to be moved along the slot to optimize the position at which a fastener assembly 34 extending through the fixture 46 into engagement with the sacrum.

In one embodiment of the invention (FIGS. 1-5), the fixture 46 positions the fastener assembly 34 so that it slopes outwardly away from the spinal plate 30 (FIG. 2) to engage the sacrum 22 only at locations which are offset to one side of the spinal plate. In another embodiment of the invention (FIGS. 6-10), the fixture 46a positions the fastener assembly 34a so that it slopes inwardly at an acute angle toward the spinal plate 30a so that the fastener 34a extends into a portion of the sacrum 24a beneath the spinal plate 30a. By selecting the proper one of the two different fixture 46 and 46a the orientation of the fastener assembly 34 or 34a relative to the sacrum can be optimized.

Having described specific preferred embodiments of the invention, the following is claimed:

1. An apparatus for maintaining a desired spatial relationship between adjacent vertebrae and the sacrum, said apparatus comprising:

elongated plate means for engaging the vertebrae and the sacrum, said elongated plate means including surface means defining a plurality of openings;

first force transmitting means extending through a first opening of the plurality of openings in said plate means for transmitting force along a first axis to connect said plate means with a vertebra;

a fixture projecting from said plate means, said fixture having a mounting end portion which is disposed in a second opening of the plurality of openings and an outer end portion which is offset to one side of said mounting end portion; and second force transmitting means extending through an opening in said outer end portion of said fixture for transmitting force along a second axis which is skewed at an acute angle relative to a plane containing the first axis and the central axis of said plate means to connect said plate means with the sacrum.

2. An apparatus as set forth in claim 1 wherein said second force transmitting means slopes outwardly away from said plate means and engages the sacrum only at a location offset to one side of said plate means.

3. An apparatus as set forth in claim 1 wherein said second force transmitting means slopes inwardly toward said plate means from a location disposed to one side of said plate means to enable said second force transmitting means to engage the sacrum at a location inwardly of said plate means.

4. An apparatus as set forth in claim 1 wherein said plate means includes an inner major side and an outer major side, said inner major side of said plate means being engageable with the vertebrae and sacrum, said outer major side of said plate means facing away from and extending generally parallel to said inner major side, said outer end portion of said fixture having a surface disposed in abutting engagement with said outer major side of said plate means.

5. An apparatus as set forth in claim 1 wherein said plurality of openings are elongated slots, and said fixture is adapted to move along said second opening.

6. An apparatus for use with an elongated plate which engages a patient's vertebrae and which elongated plate has surface means defining a plurality of openings for a first force transmitting means to extend through to transmit force along a first axis to connect the elongated plate with a vertebra, said apparatus comprising:

a one-piece fixture having a mounting end portion for receipt in an opening in the elongated plate and having an outer end portion for engaging the patient's sacrum spaced apart from said mounting end portion, said outer end portion having surface means for abuttingly engaging a portion of the elongated plate which faces away from a patient's vertebrae and an opening for second force transmitting means to extend therethrough for connecting said fixture to the sacrum, the opening in said outer end portion being disposed so the second force transmitting means is offset to one side of the elongated plate and extends at an acute angle relative to a plane containing the first axis and the longitudinal axis of the elongated plate.

7. An apparatus as set forth in claim 6 wherein said mounting end portion includes a pair of parallel side surfaces extending in a direction substantially perpendicular to said surface means of said outer end portion and being connected by a pair of opposite arcuate end portions, the lengths of said parallel side surfaces being greater than the diameters of said arcuate end portions, said parallel side surfaces being for engagement with respective inner parallel side surfaces of a longitudinally extending elongated opening defined by said surface means of the elongated plate to prevent relative rotation between said fixture and the elongated plate, the lengths of said parallel side surfaces of said mounting portion being less than the lengths of said inner parallel side surfaces of the longitudinally extending elongated opening to permit adjustment of the position of said fixture along the elongated opening.

8. An apparatus as set forth in claim 6 wherein said outer end portion includes a first flat surface, said mounting end portion includes a second flat surface extending at an acute angle to said first flat surface, the opening in said outer end portion intersecting said first flat surface and having a central axis which extends transversely to said first and second flat surfaces.

* * * * *